United States Patent [19]

Maul et al.

[11] 4,204,364
[45] May 27, 1980

[54] METHOD AND APPARATUS FOR STERILE CULTIVATION OF CELLS ON SOLID SUBSTRATES

[75] Inventors: Stephen B. Maul, Worthington; Paul A. Lemke, Cabot; Walter L. Gerner, Sarver; John B. Yoder, Butler, all of Pa.

[73] Assignee: Butler County Mushroom Farm, Inc., Worthington, Pa.

[21] Appl. No.: 934,683

[22] Filed: Aug. 18, 1978

[51] Int. Cl.$^2$ .............................................. A01G 1/04
[52] U.S. Cl. .......................................... 47/1.1; 71/5
[58] Field of Search ................................ 47/1.1; 71/5

[56] References Cited

U.S. PATENT DOCUMENTS

| | | | |
|---|---|---|---|
| 1,869,517 | 8/1932 | Sinden | 47/1.1 |
| 2,034,678 | 3/1936 | Knaust et al. | 47/1.1 |
| 2,520,318 | 8/1950 | Lescarboura | 47/1.1 |
| 2,677,917 | 5/1954 | Speakman | 47/1.1 |
| 2,723,493 | 11/1955 | Stoller | 47/1.1 |
| 2,851,821 | 9/1958 | Guichon | 47/1.1 |
| 3,177,615 | 4/1965 | Rowe | 47/1.1 |
| 3,335,521 | 8/1967 | Sohm | 47/1.1 |
| 3,938,658 | 2/1976 | Rohde | 206/439 |
| 4,059,919 | 11/1977 | Green | 47/1.1 |
| 4,063,383 | 12/1977 | Green | 47/1.1 |

Primary Examiner—Robert E. Bagwill
Attorney, Agent, or Firm—Reed, Smith, Shaw & McClay

[57] ABSTRACT

The invention disclosed comprises a process and apparatus for the cultivation of cells, and having particular application to the product of mushroom spawn, in which a particulate substrate, water and, in some cases chalk, are introduced into a rotary blender and thoroughly mixed and sterilized at a temperature of about 250° F. The mixture is cooled in the blender and a cell line inoculum is sterilely introduced into the mixture and thoroughly blended with the substrate. The blended inoculum and substrate are transferred in a sterile air flow from the blender to sterile containers which include a breathing strip in which the cells lines are incubated. The apparatus includes the combination of blender, transfer means and a clean room for filling the sterile containers.

7 Claims, 2 Drawing Figures

METHOD AND APPARATUS FOR STERILE CULTIVATION OF CELLS ON SOLID SUBSTRATES

FIELD OF THE INVENTION

The present invention relates to a method and apparatus for the production of cell lines in pure culture on a solid substrate and, in particular, to the sterile cultivation of mushroom spawn. The invention is also contemplated to be useful in the production of metabolites and anibiotics from other cell lines as well as in the cultivation of tempeh and miszo.

BACKGROUND OF THE INVENTION

The production of mushroom spawn is old and well known. For example, dry grain is placed in a bottle with water and calcium carbonate and closed with a cotton plug and sterilized. After sterilization, the bottle is cooled and the grain is inoculated with mycelium, reclosed and permitted to stand for the period of mycelium incubation. U.S. Pat. No. 1,896,517. In the cultivation of mushroom spawn sterilization of the nutrients and growing containers is very necessary in order to avoid the growth of other bacteria or molds which would inhibit the mushroom spawn.

The production of tempeh also has been known, particularly in the oriental culture, for centuries. Tempeh is fermented from soybeans inoculated with several species of Rhizopus. Recent techniques permit tempeh to be rapidly fermented in plastic bags in which the mold forms a mycelial mass binding the soybeans into a cake-like product.

Improvements in growing mushroom spawn include pre-cooking and swelling the grains to prevent their caking during sterilization, U.S. Pat. No. 2,520,318 using wood charcoal granular bases having a cereal substrate coating for growing the spawn, U.S. Pat. No. 2,677,917; and using sterilizable plastic bags for incubation of mycelia and shipping thereof, U.S. Pat. No. 2,851,821.

With respect to the method described in U.S. Pat. No. 2,851,821, elongated plastic bags are filled with the desired substrate and closed using a breathable filtering material in the mouth of the bag. The bag and contents are thereafter sterilized in much the same manner as the predecessor glass bottles, or by irradiation and inoculated with the desired inoculum and incubated. The advantages of this process include the elimination of glass bottles which were costly, fragile and cumbersome and permitted all process steps to be carried out in the bag and after incubation allowed the spawn to be transported to the growing site without removing the culture or spawn to an intermediate container. Inasmuch as plants for cultivation are relatively expensive to build and operate, they are few and far between which necessitates transporting spawn considerable distances. The advent of the plastic incubation bag represented a substantial improvement in the cultivation and transportation of mushroom spawn. Further improvements to that method were also suggested for transporting spawn. For example, U.S. Pat. No. 3,335,521 taught that the champigon spawn could be shipped in an air-tight container with ice.

Even today the preferred method of inoculating and incubating mycelia takes place in flexible plastic containers. Accordingly many advancements in the design and construction of containers have been suggested including British Patent No. 1,176,188 in which the filtering element is incorporated into the wall of the container. See also U.S. Pat. No. 3,938, 658 which teaches the use of a porous filter media over slits formed in the walls of a plastic bag. And, most recently, U.S. Pat. No. 4,063,383 which teaches growing mushroom spawn in a plastic bag having a microporous breathing panel that acts as a lining for perforations in the bag.

In conventional methods of cultivating the mushroom spawn, whether using glass bottles or plastic bags, the nutrient or substrate is normally sterilized in the container to prevent the growth of unwanted bacteria or other undesired microorganisms. These methods, however, are labor intensive. The sterilization of nutrient filled bottles or bags, the inoculation of the sterilized nutrient containers and the agitation of the individual nutrient containers to mix the inoculum during incubation requires numerous manual steps. Also, it had been heard that attempts many years ago by Somycel Company in France to sterilize and inoculate the substrate in large batches prior to filling the bottles were unsuccessful and abandoned because of contamination problems.

The present invention overcomes the problems inherent in prior art methods and reduces the labor involved in the sterilization and inoculation processes as well as minimizes the possibility of contamination during inoculation and subsequent bag filling operations. It is also an object of the present invention to eliminate the mixing steps previously required after inoculation of the nurient containers. A further object of the invention is to provide a method for producing metabolites on a solid medium rather than in a liquid fermentation process. The invention is also useful in the preparation of cultures for fermentation of food products such as tempeh. In addition to the method of the present invention, it is also an object to provide apparatus for carrying out such processes. Moreover, the invention provides apparatus wherein the sterilized nutrient is bulk inoculated, blended and sterilely discharged into sterile containers for incubation. The apparatus and method of the present invention overcome many of the obstacles encountered in cultivating cell lines on solid substrate under sterile conditions.

SUMMARY OF THE INVENTION

Generally, the method of the present invention comprises introducing a mixture of nutrients into a blender, preferably a rotary blender, which is capable of achieving and maintaining temperatures and pressures required for sterilization of the mixture. In the case of mushroom spawn, a typical mixture consists of 50 to 60% by weight grain or cereal 40 to 50% water and 1% chalk. The mixture is blended and sterilized by heating the blender to a temperature of about 252° F. or more. Preferably, steam at 15 psig is introduced into the blender during sterilization and blending. The temperature and pressure are maintained for between 35 and 120 minutes, and preferably, 45 minutes, to achieve adequate sterilization.

The blender and mixture are thereafter permitted to cool under a positive pressure of sterile air to a temperature of about 80° F. and the inoculum is sterilely transferred into the blender and thoroughly mixed with the nutrient material. After mixing is complete, the blender is connected to a bag filling station by means of a sterile connector which includes measuring means for allocating the desired amount of inoculated nutrient into bags.

The bag filling station is positioned in laminar flow of sterile air to prevent contaminants from entering the bag or connector means. Sterilized bags, each of which includes a breathing strip, are positioned at the discharge end of the connector means and filled. The filled bags are immediately sealed for incubation and delivery.

The preferred method of the present invention eliminates the difficult step of inoculating individual bags or bottles as had been done heretofore in the cultivation of mushroom spawn. Further, the method in combination with the preferred apparatus provides a sterile environment for the blending of the nutrient and inoculum. This is important in the preparation of mushroom spawn, cultures for fermentation products such as tempeh, and in growing various other cell lines.

Other advantages of the present invention will become apparent from a perusal of the following detailed description of the best mode of cultivating mushroom spawn which is to be taken in connection with the accompanying drawings.

DESCRIPTION OF THE INVENTION

Figure 1:
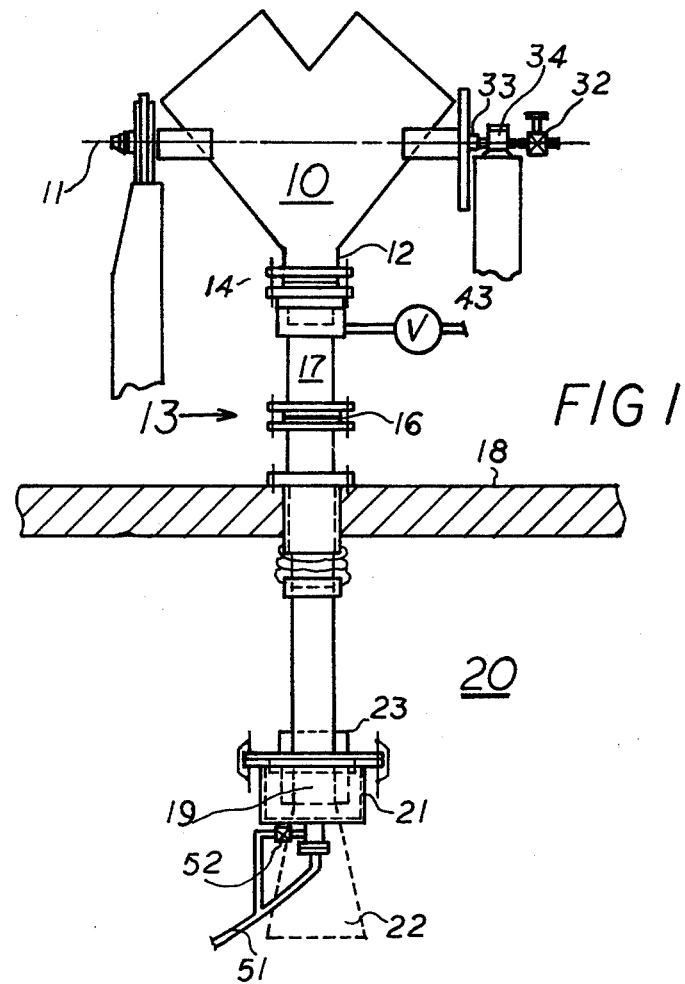
FIG. 1 is a diagrammatic elevation of the apparatus of the present invention and FIG. 2 is a schematic diagram of the Air/Stream delivery system.

With reference to FIG. 1, a rotary blender 10 is shown. Blender 10 is preferably of the type manufactured by Patterson-Kelly having a V-configuration and including conventional fluid jackets (not shown). Other types of commercially available blenders or mixers are suitable for use such as the double cone-type blenders; however, ribbon blenders and the like are not preferred because of the difficulty in cleaning and sterilizing them. Blender 10 rotates on axis 11 and includes an inlet/outlet port 12 through which the nutrient is introduced and discharged.

As shown in FIG. 1, blender 10 is provided with two openings, inlet/outlet port 12 and steam/air line 33, through which inoculum can be introduced. If the inoculum is solid or particulate in form, it is sterilely transferred through port 12 into blender 10 by gravity. Preferably port 12 is positioned at an angle above the horizontal plane through the axis of blender 10. Alternatively, a liquid inoculum is sterilely transferred through line 33 into blender 10. In both methods of inoculation, all of the connecting pipes and valves must be sterile prior to the inoculation of the nutrient to prevent contamination of the batch.

Port 12 is adapted to communicate and connect with connector means 13 through an air tight means or seal such as a Kamlok quick coupling. Any such air tight means or seal must be capable of being sterilized and of sealing pressures up to about 15 psig. Connector means 13 both measures and transports inoculated substrate to incubation bags. Connector means 13 is preferable made from stainless steel tubing and includes first and second valves 14 and 16, preferably butterfly valves. The space between valves 14 and 16 defines measuring chamber 17 having a volume which is substantially the same as the volume of the bag to be filled for incubation.

Connector means 13 is shown extending through floor 18 above filling station 20. Filling station 20 is located in a laminar flow of sterilized air preferably in an enclosed commercially available class 100 clean room. Filling station 20 includes a removable cap 21 adapted to fit over the end 19 of connector means 13 to contain steam injected into means 13 for sterilization. After connecting means 13 is sterilized, cap 21 is removed and sterilized bags 22 (shown in dashed line) are placed over discharge end 19 for filling. Positioned adjacent to the discharge end of connector means 13 is a bag sealer 23 for heat sealing the bags closed immediately after filling.

Since the method of the present invention does not require that bags 22 undergo autoclaving, it is preferable that they be made from a polyethylene film which can be gas, electron beam or radiation sterilized. Such material is substantially less expensive than the polypropylene or nylon bags of the prior art. Each bag includes a strip made from a synthetic fiber material such as Tyvek to permit the cells to breath. A Tyvek strip is positioned on each bag in a manner well known to the art.

Figure 2:
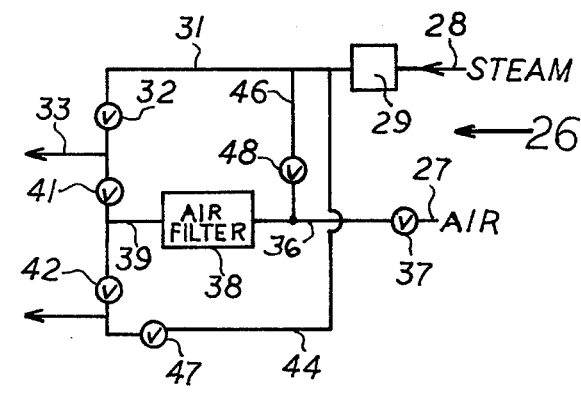

Referring to FIG. 2, a sterile air and steam system 26 is shown having a source of air 27 under pressure of about 15 psig and a source of steam 28. Steam source 28 is connected through steam trap 29 to blender 10 via line 31, valve 32 and steam inlet 33 of blender 10. Inlet 33 includes a rotary connector means 34 positioned on the axis of blender 10. Air supply source 27 is connected to line 36 through valve 37. Positioned in line 36 is filter 38 designed to sterilize the air from source 27. Preferably filter 38 is a sterilizable filter such as a Domnick Hunter Bio-x Filter, a Pall Ultipor Filter or the like. The discharge end of filter 38 is connected to line 39 which is connected to blender inlet line 33 through valve 41 and to measuring chamber 17 through valves 42 and 43. Air/Steam system 26 also includes lines 44 and 46 and associated valves 47 and 48 for supply sterilizing steam to connector means 13 and air filter 38, respectively. As part of system 26, cap 21 of filling stations 20 includes a drain 51 and steam trap 52.

In the preferred method of cultivating mushroom spawn, blender 10 is charged through port 12 with a solid substrate such as rye grain, chalk and water in conventional portions. The blender may be cold or preheated at the time of charge; however, as blending begins the jacket is heated to bring the mixture to a temperture of at least 252° F. At the same time valve 32 is opened to introduce steam at a pressure of about 15 psig into blender 10. Blending is continued at 252° F. for between 35 and 125 minutes and preferably 45 minutes. As is known in the art, the minimum time necessary to achieve sterilization of the nutrient mixture is desirable because any extra sterilization slows spawn growth.

At the completion of sterilization, the introduction of steam into the blender is discontinued and the jacket of the blender is cooled to bring the mixture to between 50° and 90° F. Preferably, the steam is released to facilitate cooling the blender. When the steam is released sterile air is introduced into the blender through inlet 33 from source 27 and filter 38 to maintain the positive pressure within the blender. After cooling, inoculum is introduced into the blender. Preferably, inoculum is sterilely transferred to the blender by gravity feed through port 12 if the inoculum is solid or through line 33 if it is a liquid. In sterilely transferring through port 12, the opening must first be sterilized and a steam of sterilized air flowing out of port 12 is necessary. It is also possible to transfer sterilized solid inoculum by means of a sterilized bomb which would attach to port 12, in which case a flow of sterilized air would not be required. Other suitable culture transfer methods may also be used.

The inoculent is thoroughly mixed with the sterilized nutrient. After mixing has been completed, connector means 13 is connected to port 12 and sterilized. Sterilization is achieved by closing discharge end 19 with cap 21 and introducing steam into connector means 13 through valves 43 and 47 and line 44. After sterilization has been completed the cap is removed and bag placed over discharge end 19. Port 12 is thereafter opened together with first valve 14 while second valve 16 is closed. The inoculated substrate is allowed to fill the volume of chamber 17 and first valve 14 closed. Valve 16 is then opened to discharge the contents of chamber 17 into bag 22 positioned over discharge end 19. Simultaneosly with opening of first valve 16, sterile air is introduced into chamber 17 to fill the space of the exiting substrate. It is also desirable to introduce sterile air into blender 10 to maintain a slight positive pressure to fill the void remaining after discharge of the mixture from the blender.

Filling of bags 22 preferably takes place in a clean room as described above, however it is possible to position filling station 20 in a laminar flow of sterilized air to prevent entrainment of any contaminants into the bag. After each bag has been filled it is sealed so that only air passing through the breathing strip enters during subsequent incubation.

While presently preferred embodiments of the best mode of the invention have been shown and described, it may be otherwise embodied within the scope of the appended claims.

What is claimed is:

1. A method for cultivation of cells on a solid substrate in a blender capable of being heated and pressurized, said method comprising:
   a. bulk blending and sterilizing in said blender a mixture of moist nutrient particles for a time and at a temperature sufficient to sterilize all of said mixture to form a uniform sterile solid substrate;
   b. cooling the sterilized substrate;
   c. while in said blender, inoculating the bulk sterilized substrate with inoculum;
   d. bulk blending the inoculum and sterilized substrate in said blender to prepare an inoculated mixture; and
   e. discharging said inoculated mixture from said blender into at least one sterile container for incubation steps c, d, and e being carried out under sterile conditions.

2. The method as set forth in claim 1 including the step of dividing the inoculated mixture into separate portions and placing each portion in a sterilized container for incubation.

3. The method as set forth in claim 2 wherein said inoculated mixture is placed in said container for incubation while causing a laminar flow of sterile air to flow around each container during placement.

4. The method as set forth in claim 2 wherein said nutrient particles consist of grain or cereal and chalk.

5. The method as set forth in claim 4 wherein said inoculum is mushroom spawn.

6. The method as set forth in claim 2 wherein said incubation containers comprise flexible plastic bags having a breathing strip thereon.

7. The method as set forth in claim 1 wherein said blending and sterilization is from between 35 and 120 minutes at a temperature of about 252° F.

* * * * *